US010440994B2

(12) United States Patent
Rostami

(10) Patent No.: US 10,440,994 B2
(45) Date of Patent: Oct. 15, 2019

(54) VAPORIZER ASSEMBLY FOR E-VAPING DEVICE

(71) Applicant: Altria Client Services LLC, Richmond, VA (US)

(72) Inventor: Ali A. Rostami, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 414 days.

(21) Appl. No.: 15/342,415

(22) Filed: Nov. 3, 2016

(65) Prior Publication Data

US 2018/0116283 A1 May 3, 2018

(51) Int. Cl.
*A61M 15/06* (2006.01)
*A24F 47/00* (2006.01)
(Continued)

(52) U.S. Cl.
CPC ......... *A24F 47/008* (2013.01); *H05B 1/0244* (2013.01); *H05B 3/03* (2013.01); *H05B 2203/021* (2013.01)

(58) Field of Classification Search
None
See application file for complete search history.

(56) References Cited

U.S. PATENT DOCUMENTS 1,474,909 A * 11/1923 Medveczky ............. F02M 1/00 219/207
2,547,865 A * 4/1951 Hanks ..................... F24H 1/106 392/337
(Continued)

FOREIGN PATENT DOCUMENTS

CN 103932401 A 7/2014
CN 203986096 U 12/2014
(Continued)

OTHER PUBLICATIONS

International Search Report and Written Opinion for corresponding European Application No. PCT/EP2017/078250 dated Feb. 20, 2018.

(Continued)

*Primary Examiner* — Thor S Campbell
(74) *Attorney, Agent, or Firm* — Harness, Dickey & Pierce, P.L.C.

(57) ABSTRACT

A vaporizer assembly for an e-vaping device includes a heater coil structure, a set of electrical lead structures coupled to opposite ends of the heater coil structure, and a non-conductive connector structure connected to each of the electrical lead structures, such that the electrical lead structures are coupled together independently of the heater coil structure. The vaporizer assembly may contact a dispensing interface structure through the heater coil structure. The vaporizer assembly may heat pre-vapor formulation drawn from a reservoir by the dispensing interface. The heater coil structure may define a surface, and the vaporizer assembly may apply a mechanical force to the dispensing interface structure, such that the heater coil structure is in compression with the dispensing interface structure and the heater coil structure surface is substantially flush with a surface of the dispensing interface structure. The heater coil structure may define a three-dimensional surface.

14 Claims, 7 Drawing Sheets

(51) Int. Cl.
*H05B 1/02* (2006.01)
*H05B 3/03* (2006.01)

(56) References Cited

U.S. PATENT DOCUMENTS

| | | | | |
|---|---|---|---|---|
| 5,796,914 | A * | 8/1998 | Gatzemeyer | A01M 1/2077 392/390 |
| 9,603,386 | B2 * | 3/2017 | Xiang | A24F 47/008 |
| 9,675,114 | B2 * | 6/2017 | Timmermans | A24F 47/008 |
| 9,808,032 | B2 * | 11/2017 | Yamada | A24F 47/008 |
| 2012/0090630 | A1 * | 4/2012 | Hon | A24F 47/002 131/273 |
| 2012/0199146 | A1 | 8/2012 | Marangos | |
| 2013/0152922 | A1 | 6/2013 | Benassayag et al. | |
| 2013/0192619 | A1 | 8/2013 | Tucker et al. | |
| 2013/0192623 | A1 | 8/2013 | Tucker et al. | |
| 2013/0313246 | A1 * | 11/2013 | Long | H05B 3/48 219/544 |
| 2014/0060554 | A1 * | 3/2014 | Collett | H05B 3/265 131/328 |
| 2014/0224244 | A1 | 8/2014 | Liu | |
| 2014/0238423 | A1 | 8/2014 | Tucker et al. | |
| 2014/0253144 | A1 * | 9/2014 | Novak, III | A24F 47/008 324/550 |
| 2014/0305454 | A1 | 10/2014 | Rinker et al. | |
| 2014/0314397 | A1 | 10/2014 | Alima | |
| 2015/0020823 | A1 | 1/2015 | Lipowicz et al. | |
| 2015/0217068 | A1 * | 8/2015 | Wakalopulos | A61M 15/06 128/202.21 |
| 2015/0313275 | A1 | 11/2015 | Anderson et al. | |
| 2016/0000146 | A1 | 1/2016 | Zhu | |
| 2016/0007655 | A1 | 1/2016 | Li | |
| 2016/0106153 | A1 | 4/2016 | Zhu | |
| 2016/0106154 | A1 | 4/2016 | Lord | |
| 2016/0157523 | A1 * | 6/2016 | Liu | A24F 47/008 392/395 |
| 2016/0286865 | A1 | 10/2016 | King et al. | |
| 2017/0020192 | A1 * | 1/2017 | Fregonese | H05B 3/0014 |
| 2017/0035109 | A1 | 2/2017 | Liu | |
| 2017/0135402 | A1 * | 5/2017 | Zitzke | A24F 47/008 |
| 2017/0172212 | A1 * | 6/2017 | Phillips | A24F 47/008 |
| 2017/0215485 | A1 * | 8/2017 | Zitzke | A24F 47/008 |
| 2018/0042301 | A1 * | 2/2018 | Rostami | A24F 47/008 |
| 2018/0279672 | A1 * | 10/2018 | Davis | A24F 47/008 |

FOREIGN PATENT DOCUMENTS

| | | | |
|---|---|---|---|
| EP | 2460424 | A1 | 6/2012 |
| EP | 2641490 | A1 | 9/2013 |
| KR | 101355794 | B1 | 1/2014 |
| WO | WO-2014012894 | A1 | 1/2014 |
| WO | WO-2015149405 | A1 | 10/2015 |
| WO | WO-2015198015 | A1 | 12/2015 |

OTHER PUBLICATIONS

International Preliminary Report on Patentability dated Feb. 15, 2019 for corresponding International Application No. PCT/EP2017/078250.

* cited by examiner

VAPORIZER ASSEMBLY FOR E-VAPING DEVICE

BACKGROUND

Field

One or more example embodiments relate to electronic vaping and/or e-vaping devices.

Description of Related Art

E-vaping devices, also referred to herein as electronic vaping devices (EVDs) may be used by adult vapers for portable vaping. Flavored vapors within an e-vaping device may be used to deliver a flavor along with the vapor that may be produced by the e-vaping device.

In some cases, e-vaping devices may hold pre-vapor formulations within a reservoir and may form a vapor based on drawing pre-vapor formulation from the reservoir and applying heat to the drawn pre-vapor formulation to vaporize same.

In some cases, e-vaping devices may be manufactured via mass-production. Such mass-production may be at least partially automated.

SUMMARY

According to some embodiments, a vaporizer assembly for an e-vaping device may include a heater coil structure, a set of two electrical lead structures, and a non-conductive connector structure. The electrical lead structures may be coupled to opposite ends of the heater coil structure. The non-conductive connector structure may be connected to each of the electrical lead structures, such that the electrical lead structures are coupled together independently of the heater coil structure.

The vaporizer assembly may be configured to contact a dispensing interface structure through the heater coil structure, such that the vaporizer assembly is configured to heat pre-vapor formulation drawn from a reservoir by the dispensing interface structure.

The vaporizer assembly may be configured to contact the dispensing interface structure such that the heater coil structure is at least partially within an interior space of the dispensing interface structure.

The heater coil structure may define a surface, and the vaporizer assembly may be configured to apply a mechanical force to the dispensing interface structure, such that the heater coil structure is in compression with the dispensing interface structure and the heater coil structure surface is substantially flush with a surface of the dispensing interface structure.

The vaporizer assembly may be configured to contact the dispensing interface structure, such that the dispensing interface structure is between the heater coil structure and the non-conductive connector structure.

The heater coil structure may define a three-dimensional (3-D) surface.

The 3-D surface may be a substantially conical surface.

At least one electrical lead structure, of the set of two electrical lead structures, may include an interior portion and a surface portion, and the surface portion may be associated with a reduced conductivity, in relation to the interior portion.

According to some example embodiments, a cartridge for an e-vaping device may include a reservoir configured to hold a pre-vapor formulation, a dispensing interface structure coupled to the reservoir, the dispensing interface configured to draw the pre-vapor formulation from the reservoir, and a vaporizer assembly in contact with the dispensing interface structure, the vaporizer assembly configured to heat the drawn pre-vapor formulation. The vaporizer assembly may include a heater coil structure, a set of two electrical lead structures, and a non-conductive connector structure. The electrical lead structures may be coupled to opposite ends of the heater coil structure. The non-conductive connector structure may be connected to each of the electrical lead structures, such that the electrical lead structures are coupled together independently of the heater coil structure.

The heater coil structure may be at least partially within an interior space of the dispensing interface structure.

The heater coil structure may define a surface, and the vaporizer assembly may be configured to apply a mechanical force to the dispensing interface structure, such that the heater coil structure is in compression with the dispensing interface structure, and the heater coil structure surface is substantially flush with a surface of the dispensing interface structure.

The dispensing interface structure may be between the heater coil structure and the non-conductive connector structure.

The heater coil structure may define a three-dimensional (3-D) surface.

The 3-D surface may be a substantially conical surface.

At least one electrical lead structure, of the set of two electrical lead structures, may include an interior portion and a surface portion, and the surface portion may be associated with a reduced conductivity, in relation to the interior portion.

According to some example embodiments, an e-vaping device may include a cartridge and a power supply section coupled to the cartridge. The cartridge may include a reservoir configured to hold a pre-vapor formulation, a dispensing interface structure coupled to the reservoir, the dispensing interface configured to draw the pre-vapor formulation from the reservoir, and a vaporizer assembly in contact with the dispensing interface structure, the vaporizer assembly configured to heat the drawn pre-vapor formulation. The vaporizer assembly may include a heater coil structure, a set of two electrical lead structures, and a non-conductive connector structure. The electrical lead structures may be coupled to opposite ends of the heater coil structure. The non-conductive connector structure may be connected to each of the electrical lead structures, such that the electrical lead structures are coupled together independently of the heater coil structure. The power supply section may be configured to supply electrical power to the vaporizer assembly.

The heater coil structure may be at least partially within an interior space of the dispensing interface structure.

The heater coil structure may define a surface, and the vaporizer assembly may be configured to apply a mechanical force to the dispensing interface structure, such that the heater coil structure is in compression with the dispensing interface structure, and the heater coil structure surface is substantially flush with a surface of the dispensing interface structure.

The dispensing interface structure may be between the heater coil structure and the non-conductive connector structure.

The heater coil structure may define a three-dimensional (3-D) surface.

The 3-D surface may be a substantially conical surface.

The power supply section may include a rechargeable battery.

The cartridge and the power supply section may be removably coupled together.

At least one electrical lead structure, of the set of two electrical lead structures, may include an interior portion and a surface portion, and the surface portion may be associated with a reduced conductivity, in relation to the interior portion.

BRIEF DESCRIPTION OF THE DRAWINGS

The various features and advantages of the non-limiting embodiments described herein become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION OF EXAMPLE EMBODIMENTS

Figure 1A:
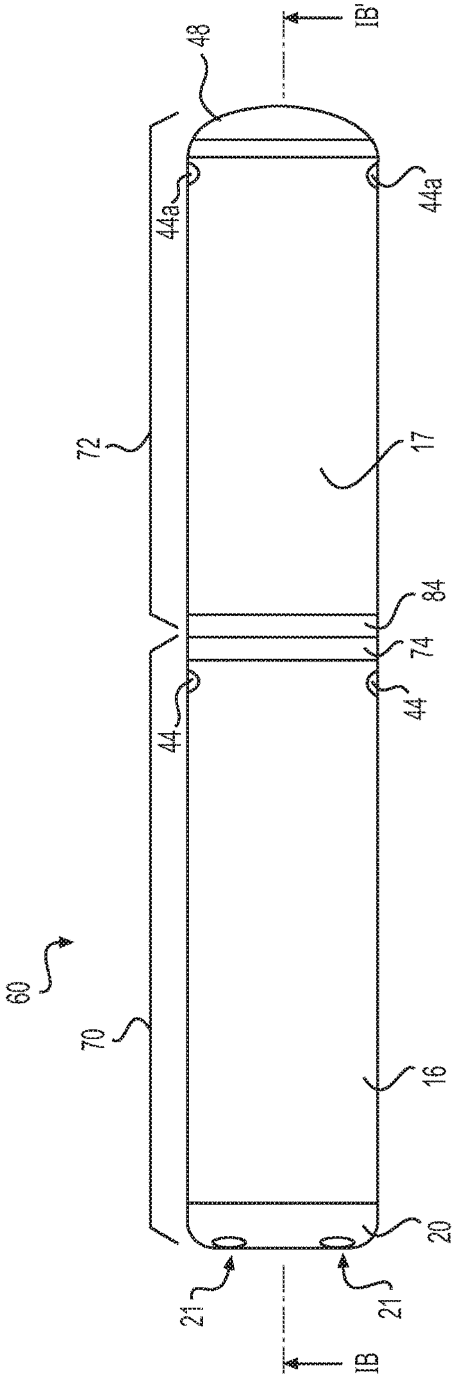
FIG. 1A is a side view of an e-vaping device according to some example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances and/or material tolerances, are to be expected. As described herein, an element having "substantially" a certain characteristic will be understood to include an element having the certain characteristics within the bounds of manufacturing techniques and/or tolerances and/or material tolerances. For example, an element that is "substantially cylindrical" in shape will be understood to be cylindrical within the bounds of manufacturing techniques and/or tolerances and/or material tolerances. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Figure 1B:
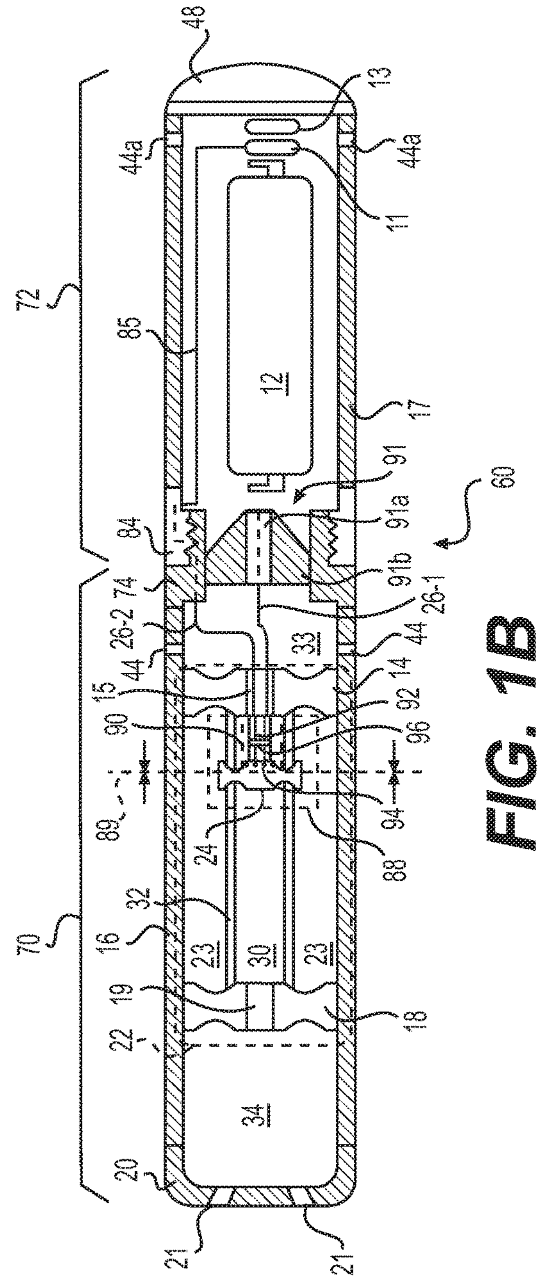
FIG. 1B is a cross-sectional view along line IB-IB' of the e-vaping device of FIG. 1A.

FIG. 1A is a side view of an e-vaping device 60 according to some example embodiments. FIG. 1B is a cross-sectional view along line IB-IB' of the e-vaping device of FIG. 1A. The e-vaping device 60 may include one or more of the features set forth in U.S. Patent Application Publication No. 2013/0192623 to Tucker et al. filed Jan. 31, 2013 and U.S. Patent Application Publication No. 2013/0192619 to Tucker et al. filed Jan. 14, 2013, the entire contents of each of which are incorporated herein by reference thereto. As used herein, the term "e-vaping device" is inclusive of all types of electronic vaping devices, regardless of form, size or shape.

Referring to FIG. 1A and FIG. 1B, an e-vaping device 60 includes a replaceable cartridge (or first section) 70 and a reusable power supply section (or second section) 72. Sections 70, 72 are removably coupled together at complementary interfaces 74, 84 of the respective cartridge 70 and power supply section 72.

In some example embodiments, the interfaces 74, 84 are threaded connectors. It should be appreciated that each interface 74, 84 may be any type of connector, including a snug-fit, detent, clamp, bayonet, and/or clasp. One or more of the interfaces 74, 84 may include a cathode connector, anode connector, some combination thereof, etc. to electrically couple one or more elements of the cartridge 70 to one or more power supplies 12 in the power supply section 72 when the interfaces 74, 84 are coupled together.

As shown in FIG. 1A and FIG. 1B, in some example embodiments, an outlet end insert 20 is positioned at an outlet end of the cartridge 70. The outlet end insert 20 includes at least one outlet port 21 that may be located off-axis from the longitudinal axis of the e-vaping device 60. The at least one outlet port 21 may be angled outwardly in relation to the longitudinal axis of the e-vaping device 60. Multiple outlet ports 21 may be uniformly or substantially uniformly (e.g., uniformly within the bounds of manufacturing techniques and/or tolerances and/or material tolerances) distributed about the perimeter of the outlet end insert 20 so as to uniformly or substantially uniformly distribute a vapor drawn through the outlet end insert 20 during vaping. Thus, as a vapor is drawn through the outlet end insert 20, the vapor may move in different directions.

The cartridge 70 includes a vapor generator 22. The vapor generator 22 includes at least a portion of an outer housing 16 of the cartridge 70 extending in a longitudinal direction and an inner tube 32 coaxially positioned within the outer housing 16. The power supply section 72 includes an outer housing 17 extending in a longitudinal direction. In some example embodiments, the outer housing 16 may be a single tube housing both the cartridge 70 and the power supply section 72. In the example embodiment illustrated in FIG. 1A and FIG. 1B, the entire e-vaping device 60 may be disposable.

The outer housings 16, 17 may each have a generally cylindrical cross-section. In some example embodiments, the outer housings 16, 17 may each have a generally triangular cross-section along one or more of the cartridge 70 and the power supply section 72. In some example embodiments, the outer housing 17 may have a greater circumference or dimensions at a tip end than a circumference or dimensions of the outer housing 16 at an outlet end of the e-vaping device 60.

At one end of the inner tube 32, a nose portion of a gasket (or seal) 14 is fitted into an end portion of the inner tube 32. An outer perimeter of the gasket 14 provides a substantially airtight seal (e.g., airtight within the bounds of manufacturing techniques and/or tolerances and/or material tolerances) with an interior surface of the outer housing 16. The gasket 14 includes a channel 15. The channel 15 opens into an interior of the inner tube 32 that defines a central channel 30. A space 33 at a backside portion of the gasket 14 assures communication between the channel 15 and one or more air inlet ports 44. Air may be drawn into the space 33 in the cartridge 70 through the one or more air inlet ports 44 during vaping, and the channel 15 may enable such air to be drawn into the central channel 30 of the vapor generator 22.

In some example embodiments, a nose portion of another gasket 18 is fitted into another end portion of the inner tube 32. An outer perimeter of the gasket 18 provides a substantially airtight seal with an interior surface of the outer housing 16. The gasket 18 includes a channel 19 disposed between the central channel 30 of the inner tube 32 and a space 34 at an outlet end of the outer housing 16. The channel 19 may transport a vapor from the central channel 30 to exit the vapor generator 22 to the space 34. The vapor may exit the cartridge 70 from space 34 through the outlet end insert 20.

In some example embodiments, at least one air inlet port 44 is formed in the outer housing 16, adjacent to the interface 74 to reduce and/or minimize the chance of an adult vaper's fingers occluding one of the ports and to control the resistance-to-draw (RTD) during vaping. In some example embodiments, the air inlet ports 44 may be machined into the outer housing 16 with precision tooling such that their diameters are closely controlled and replicated from one e-vaping device 60 to the next during manufacture.

In a further example embodiment, the air inlet ports 44 may be drilled with carbide drill bits or other high-precision tools and/or techniques. In yet a further example embodiment, the outer housing 16 may be formed of metal or metal alloys such that the size and shape of the air inlet ports 44 may not be altered during manufacturing operations, packaging, and/or vaping. Thus, the air inlet ports 44 may provide more consistent RTD. In yet a further example embodiment, the air inlet ports 44 may be sized and configured such that the e-vaping device 60 has a RTD in the range of from about 60 mm $H_2O$ to about 150 mm $H_2O$.

Still referring to FIG. 1A and FIG. 1B, the vapor generator 22 includes a reservoir 23. The reservoir 23 is configured to hold one or more pre-vapor formulations. The reservoir 23 is contained in an outer annulus between the inner tube 32 and the outer housing 16 and between the gaskets 14 and 18. Thus, the reservoir 23 at least partially surrounds the central channel 30. The reservoir 23 may include a storage medium configured to store the pre-vapor formulation therein. A storage medium included in a reservoir 23 may include a winding of cotton gauze or other fibrous material about a portion of the cartridge 70.

In some example embodiments, the reservoir 23 is configured to hold different pre-vapor formulations. For example, the reservoir 23 may include one or more sets of storage media, where the one or more sets of storage media are configured to hold different pre-vapor formulations.

A pre-vapor formulation, as described herein, is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or pre-vapor formulation such as glycerin and propylene glycol. Different pre-vapor formulations may include different elements. Different pre-vapor formulations may have different properties. For example, different pre-vapor formulations may have different viscosities when the different pre-vapor formulations are at a common temperature. One or more of pre-vapor formulations may include those described in U.S. Patent Application Publication No. 2015/0020823 to Lipowicz et al. filed Jul. 16, 2014 and U.S. Patent Application Publication No. 2015/0313275 to Anderson et al. filed Jan. 21, 2015, the entire contents of each of which is incorporated herein by reference thereto.

Figure 2A:
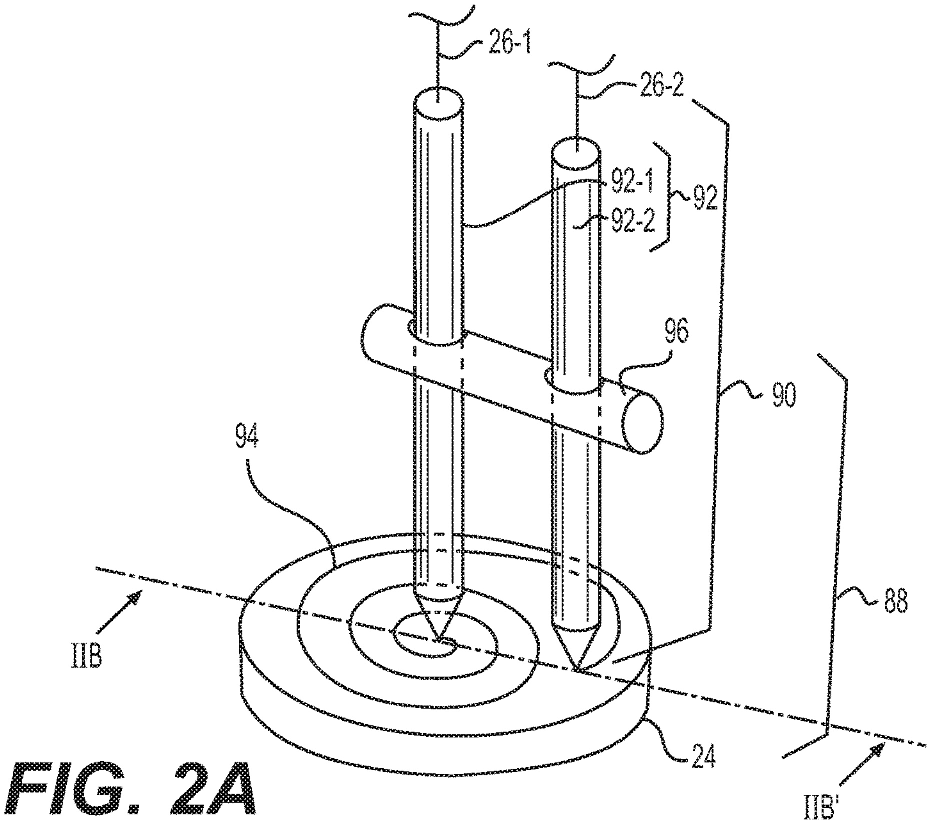
FIG. 2A is a perspective view of a vaporizer assembly including a heater coil structure that defines a planar surface, according to some example embodiments.
Figure 2B:
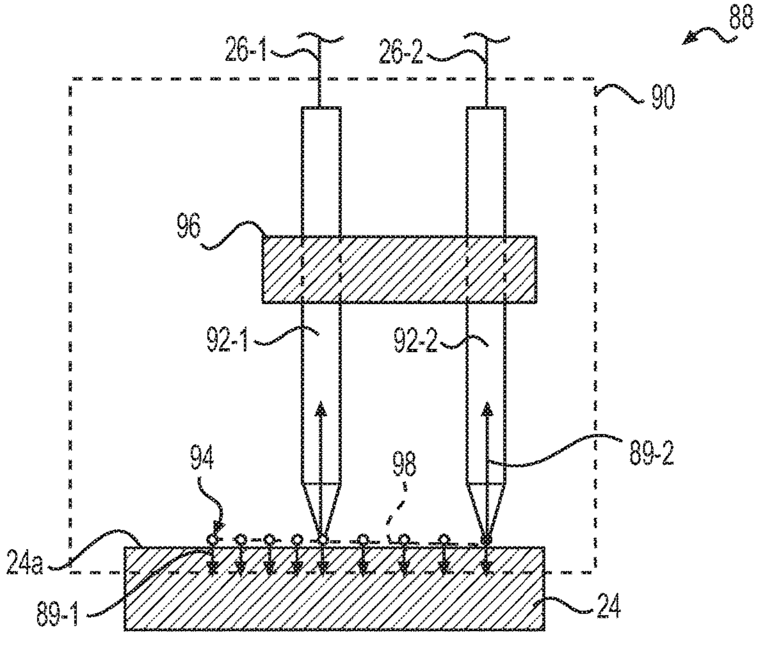
FIG. 2B is a cross-sectional view along line IIB-IIB' of the vaporizer assembly of FIG. 2A.

Still referring to FIG. 1A and FIG. 1B, the vapor generator 22 includes a vaporizer assembly 88. The vaporizer assembly 88, described further below with regard to at least FIGS. 2A-2B, is configured to vaporize at least a portion of the pre-vapor formulation held in the reservoir 23 to form a vapor.

Still referring to FIG. 1A and FIG. 1B, the vaporizer assembly 88 includes a dispensing interface structure 24. The dispensing interface structure 24 may be coupled to the reservoir 23. The dispensing interface structure 24 is configured to draw one or more pre-vapor formulations from the reservoir 23. Pre-vapor formulation drawn from the reservoir 23 into the dispensing interface structure 24 may be drawn into an interior of the dispensing interface structure 24. It will be understood, therefore, that pre-vapor formulation drawn from a reservoir 23 into a dispensing interface structure 24 may include pre-vapor formulation held in the dispensing interface structure 24.

In some example embodiments, the dispensing interface structure 24 includes a porous material that is configured to receive and hold pre-vapor formulation. The porous material may include an absorbent material. The porous material may include a paper material. In some example embodiments, the porous material includes a ceramic paper material, such that the dispensing interface structure 24 includes a ceramic paper material. The dispensing interface structure 24 may include a porous material that is hydrophilic. The porous material may be about 1/64 inches in thickness. In some example embodiments, the porous material may include a wick having an elongated form. The wick may include a wicking material. The wicking material may be a fibrous wicking material. In some example embodiments, at least a portion of the dispensing interface structure 24 may extend into reservoir 23, such that the dispensing interface structure 24 is in fluid communication with pre-vapor formulation within the reservoir 23.

Still referring to FIG. 1A and FIG. 1B, the vaporizer assembly 88 includes a heater assembly 90. The heater assembly 90 includes a set of electrical lead structures 92, a heater coil structure 94, and a non-conductive connector structure 96. The structure of the heater assembly 90 and elements included therein is described further below with reference to at least FIGS. 2A-2B.

As described further below with regard to at least FIGS. 2A-2B, the heater assembly 90 may be in contact with one or more surfaces of the dispensing interface structure 24. In some example embodiments, the heater assembly 90 may be directly coupled to the dispensing interface structure 24 such that the heater assembly 90 is coupled to an exterior surface of the dispensing interface structure 24.

The heater assembly 90 may be in contact with the dispensing interface structure 24 such that at least a portion of the heater coil structure 94 contacts a surface of the dispensing interface structure 24.

In some example embodiments, the heater assembly 90 may exert ("apply") a mechanical force 89 on the dispensing interface structure 24, such that the dispensing interface structure 24 and at least a portion of the heater assembly 90 are in compression with each other. Based on heater assembly 90 applying a mechanical force 89 on the dispensing interface structure 24, heat transfer between the heater assembly 90 and the dispensing interface structure 24 may be improved through improved physical contact therebetween. As a result, the magnitude of vapor generation according to a given magnitude of electrical power supply (e.g., vapor generation efficiency) in the cartridge 70 may be improved, based at least in part upon the heater assembly 90 exerting the mechanical force 89 on the dispensing interface structure 24.

Referring back to the example embodiments illustrated in FIGS. 1A-1B, if and/or when the heater assembly 90 is activated, one or more pre-vapor formulations in the dispensing interface structure 24 may be vaporized by the heater assembly 90 to form a vapor. Activation of the heater assembly 90 may include supplying electrical power to the heater assembly 90 (e.g., inducing an electrical current through one or more portions of the heater assembly 90) to cause one or more portions of the heater assembly 90, including the heater coil structure 94, to generate heat based on the supplied electrical power.

In some example embodiments, including the example embodiments shown in FIG. 1B, and as shown further with reference to at least FIG. 2A and FIG. 2B, the heater coil structure 94 includes a heater coil wire that is configured to contact at least one exterior surface of the dispensing interface structure 24. The heater coil structure 94 may heat one or more portions of the dispensing interface structure 24, including at least some of the pre-vapor formulation held in the dispensing interface structure 24, to vaporize the at least some of the pre-vapor formulation held in the dispensing interface structure 24.

The heater coil structure 94 may heat one or more pre-vapor formulations in the dispensing interface structure 24 through thermal conduction. Alternatively, heat from the heater coil structure 94 may be conducted to the one or more pre-vapor formulations by a heated conductive element or the heater coil structure 94 may transfer heat to the incoming ambient air that is drawn through the e-vaping device 60 during vaping. The heated ambient air may heat the pre-vapor formulation by convection.

The pre-vapor formulation drawn from the reservoir 23 into the dispensing interface structure 24 may be vaporized from the dispensing interface structure 24 based on heat generated by the heater assembly 90. During vaping, pre-vapor formulation may be transferred from the reservoir 23 and/or storage medium in the proximity of the heater coil structure 94 through capillary action of the dispensing interface structure 24.

Still referring to FIG. 1A and FIG. 1B, in some example embodiments, the cartridge 70 includes a connector element 91. Connector element 91 may include one or more of a cathode connector element and an anode connector element. In the example embodiment illustrated in FIG. 1B, for example, electrical lead 26-1 is coupled to the connector element 91. As further shown in FIG. 1B, the connector element 91 is configured to couple with a power supply 12 included in the power supply section 72. If and/or when interfaces 74, 84 are coupled together, the connector element 91 and power supply 12 may be coupled together. Coupling connector element 91 and power supply 12 together may electrically couple electrical lead 26-1 and power supply 12 together.

In some example embodiments, one or more of the interfaces 74, 84 include one or more of a cathode connector element and an anode connector element. In the example embodiment illustrated in FIG. 1B, for example, electrical lead 26-2 is coupled to the interface 74. As further shown in FIG. 1B, the power supply section 72 includes an electrical lead 85 that couples the control circuitry 11 to the interface 84. If and/or when interfaces 74, 84 are coupled together, the coupled interfaces 74, 84 may electrically couple electrical leads 26-2 and 85 together.

If and/or when interfaces 74, 84 are coupled together, one or more electrical circuits through the cartridge 70 and power supply section 72 may be established. The established electrical circuits may include at least the heater assembly 90, the control circuitry 11, and the power supply 12. The electrical circuit may include electrical leads 26-1 and 26-2, electrical lead 85, and interfaces 74, 84.

The connector element 91 may include an insulating material 91*b* and a conductive material 91*a*. The conductive material 91*a* may electrically couple electrical lead 26-1 to power supply 12, and the insulating material 91*b* may insulate the conductive material 91*a* from the interface 74, such that a probability of an electrical short between the electrical lead 26-1 and the interface 74 is reduced and/or prevented. For example, if and/or when the connector element 91 includes a cylindrical cross-section orthogonal to a longitudinal axis of the e-vaping device 60, the insulating material 91*b* included in connector element 91 may be in an outer annular portion of the connector element 91 and the conductive material 91*a* may be in an inner cylindrical portion of the connector element 91, such that the insulating material 91*b* surrounds the conductive material 91*a* and reduces and/or prevents a probability of an electrical connection between the conductive material 91*a* and the interface 74.

Still referring to FIG. 1A and FIG. 1B, the power supply section 72 includes a sensor 13 responsive to air drawn into the power supply section 72 through an air inlet port 44*a* adjacent to a free end or tip end of the e-vaping device 60, a power supply 12, and control circuitry 11. In some example embodiments, including the example embodiment illustrated in FIG. 1B, the sensor 13 may be coupled to control circuitry 11. The power supply 12 may include a rechargeable battery. The sensor 13 may be one or more of a pressure sensor, a microelectromechanical system (MEMS) sensor, etc.

In some example embodiments, the power supply 12 includes a battery arranged in the e-vaping device 60 such that the anode is downstream of the cathode. A connector element 91 contacts the downstream end of the battery. The heater assembly 90 is coupled to the power supply 12 by at least the two spaced apart electrical leads 26-1 to 26-2.

The power supply 12 may be a Lithium-ion battery or one of its variants, for example a Lithium-ion polymer battery. Alternatively, the power supply 12 may be a nickel-metal hydride battery, a nickel cadmium battery, a lithium-manganese battery, a lithium-cobalt battery or a fuel cell. The e-vaping device 60 may be usable by an adult vaper until the energy in the power supply 12 is depleted or in the case of lithium polymer battery, a minimum voltage cut-off level is achieved. Further, the power supply 12 may be rechargeable and may include circuitry configured to allow the battery to be chargeable by an external charging device. To recharge the e-vaping device 60, a Universal Serial Bus (USB) charger or other suitable charger assembly may be used.

Still referring to FIG. 1A and FIG. 1B, upon completing the connection between the cartridge 70 and the power supply section 72, the power supply 12 may be electrically connected with the heater assembly 90 of the cartridge 70 upon actuation of the sensor 13. The interfaces 74, 84 may be configured to removably couple the cartridge 70 and power supply section 72 together. Air is drawn primarily into the cartridge 70 through one or more air inlet ports 44. The one or more air inlet ports 44 may be located along the outer housing 16 or at one or more of the interfaces 74, 84.

In some example embodiments, the sensor 13 is configured to generate an output indicative of a magnitude and direction of airflow in the e-vaping device 60. The control circuitry 11 receives the output of the sensor 13, and determines if (1) a direction of the airflow in flow communication with the sensor 13 indicates a draw on the outlet-end insert 20 (e.g., a flow through the outlet-end insert 20 towards an exterior of the e-vaping device 60 from the central channel 30) versus blowing (e.g., a flow through the outlet-end insert 20 from an exterior of the e-vaping device 60 towards the central channel 30) and (2) the magnitude of the draw (e.g., flow velocity, volumetric flow rate, mass flow rate, some combination thereof, etc.) exceeds a threshold level. If and/or when the control circuitry 11 determines that the direction of the airflow in flow communication with the sensor 13 indicates a draw on the outlet-end insert 20 (e.g., a flow through the outlet-end insert 20 towards an exterior of the e-vaping device 60 from the central channel 30) versus blowing (e.g., a flow through the outlet-end insert 20 from an exterior of the e-vaping device 60 towards the central channel 30) and the magnitude of the draw (e.g., flow velocity, volumetric flow rate, mass flow rate, some combination thereof, etc.) exceeds a threshold level, the control circuitry 11 may electrically connect the power supply 12 to the heater assembly 90, thereby activating the heater assembly 90. Namely, the control circuitry 11 may selectively electrically connect the electrical leads 26-1, 26-2, and 85 in a closed electrical circuit (e.g., by activating a heater power control circuit included in the control circuitry 11) such that the heater assembly 90 becomes electrically connected to the power supply 12. In some example embodiments, the sensor 13 may indicate a pressure drop, and the control circuitry 11 may activate the heater assembly 90 in response thereto.

In some example embodiments, the control circuitry 11 may include a time-period limiter. In some example embodiments, the control circuitry 11 may include a manually operable switch for an adult vaper to initiate heating. The time-period of the electric current supply to the heater assembly 90 may be set or pre-set depending on the amount of pre-vapor formulation desired to be vaporized. In some example embodiments, the sensor 13 may detect a pressure drop and the control circuitry 11 may supply power to the heater assembly 90 as long as heater activation conditions are met. Such conditions may include one or more of the sensor 13 detecting a pressure drop that at least meets a threshold magnitude, the control circuitry 11 determining that a direction of the airflow in flow communication with the sensor 13 indicates a draw on the outlet-end insert 20 (e.g., a flow through the outlet-end insert 20 towards an exterior of the e-vaping device 60 from the central channel 30) versus blowing (e.g., a flow through the outlet-end insert 20 from an exterior of the e-vaping device 60 towards the central channel 30), and the magnitude of the draw (e.g., flow velocity, volumetric flow rate, mass flow rate, some combination thereof, etc.) exceeds a threshold level.

TAs shown in the example embodiment illustrated in FIG. 1B, some example embodiments of the power supply section 72 include a heater activation light 48 configured to glow when the heater assembly 90 is activated. The heater activation light 48 may include a light emitting diode (LED). Moreover, the heater activation light 48 may be arranged to be visible to an adult vaper during vaping. In addition, the heater activation light 48 may be utilized for e-vaping system diagnostics or to indicate that recharging is in progress. The heater activation light 48 may also be configured such that the adult vaper may activate and/or deactivate the heater activation light 48 for privacy. As shown in FIG. 1A and FIG. 1B, the heater activation light 48 may be located on the tip end of the e-vaping device 60. In some example embodiments, the heater activation light 48 may be located on a side portion of the outer housing 17.

In addition, the at least one air inlet port 44*a* may be located adjacent to the sensor 13, such that the sensor 13 may sense air flow indicative of vapor being drawn through the outlet end of the e-vaping device 60. The sensor 13 may activate the power supply 12 and the heater activation light 48 to indicate that the heater assembly 90 is activated.

In some example embodiments, the control circuitry 11 may control the supply of electrical power to the heater assembly 90 responsive to the sensor 13. In some example embodiments, the control circuitry 11 is configured to adjustably control the electrical power supplied to the heater assembly 90. Adjustably controlling the supply of electrical power may include controlling the supply of electrical power such that supplied electrical power has a determined set of characteristics, where the determined set of characteristics may be adjusted. To adjustably control the supply of electrical power, the control circuitry 11 may control the supply of electrical power such that electrical power having one or more characteristics determined by the control circuitry 11 is supplied to the heater assembly 90. Such one or more selected characteristics may include one or more of voltage and current of the electrical power. Such one or more selected characteristics may include a magnitude of the electrical power. It will be understood that adjustably controlling the supply of electrical power may include determining a set of characteristics of electrical power and controlling the supply of electrical power such that electrical power supplied to the heater assembly 90 has the determined set of characteristics.

In some example embodiments, the control circuitry 11 may include a maximum, time-period limiter. In some example embodiments, the control circuitry 11 may include a manually operable switch for an adult vaper to initiate a vaping. The time-period of the electric current supply to the heater assembly 90 may be given, or alternatively pre-set (e.g., prior to controlling the supply of electrical power to the heater assembly 90), depending on the amount of pre-vapor formulation desired to be vaporized. In some example embodiments, the control circuitry 11 may control the supply of electrical power to the heater assembly 90 as long as the sensor 13 detects a pressure drop.

To control the supply of electrical power to heater assembly 90, the control circuitry 11 may execute one or more instances of computer-executable program code. The control circuitry 11 may include a processor and a memory. The memory may be a computer-readable storage medium storing computer-executable code.

The control circuitry 11 may include processing circuitry including, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuitry 11 may be at least one of an application-specific integrated circuit (ASIC) and an ASIC chip.

The control circuitry 11 may be configured as a special purpose machine by executing computer-readable program code stored on a storage device. The program code may include program or computer-readable instructions, software elements, software modules, data files, data structures, and/or the like, capable of being implemented by one or more hardware devices, such as one or more of the control circuitry mentioned above. Examples of program code include both machine code produced by a compiler and higher level program code that is executed using an interpreter.

The control circuitry 11 may include one or more electronic storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a USB flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device through a network interface, rather than through a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, through a wired interface, an air interface, and/or any other like medium.

The control circuitry 11 may be a special purpose machine configured to execute the computer-executable code to control the supply of electrical power to heater assembly 90. In some example embodiments, an instance of computer-executable code, when executed by the control circuitry 11, causes the control circuitry 11 to control the supply of electrical power to heater assembly 90 according to an activation sequence. Controlling the supply of electrical power to heater assembly 90 may be referred to herein interchangeably as activating the heater assembly 90, activating the one or more heater coil structures 94 included in the heater assembly 90, some combination thereof, or the like.

Still referring to FIG. 1A and FIG. 1B, when at least one of the heater assembly 90 and the heater coil structure 94 is activated, the heater coil structure 94 may heat at least a portion of the dispensing interface structure 24 in contact with at least one portion of the heater assembly 90, including at least a portion of the dispensing interface structure 24 in contact with the heater coil structure 94, for less than about 10 seconds. Thus, the power cycle (or maximum vaping length) may range in period from about 2 seconds to about 10 seconds (e.g., about 3 seconds to about 9 seconds, about 4 seconds to about 8 seconds or about 5 seconds to about 7 seconds).

In some example embodiments, at least one portion of the heater assembly 90, including the heater coil structure 94, the electrical lead structures 92, some combination thereof, or the like are electrically coupled to the control circuitry 11. The control circuitry 11 may adjustably control the supply of electrical power to the heater assembly 90 to control an amount of heat generated by one or more portions of the heater assembly 90.

The pre-vapor formulation may include nicotine or may exclude nicotine. The pre-vapor formulation may include one or more tobacco flavors. The pre-vapor formulation may include one or more flavors that are separate from one or more tobacco flavors.

In some example embodiments, a pre-vapor formulation that includes nicotine may also include one or more acids. The one or more acids may be one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-penenoic acid, phenylacetic acid, 3-phenylpropionic acid, hydrochloric acid, phosphoric acid, sulfuric acid and combinations thereof.

The storage medium of one or more reservoirs 23 may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section that has a Y-shape, cross shape, clover shape or any other suitable shape. In some example embodiments, one or more reservoirs 23 may include a filled tank lacking any storage medium and containing only pre-vapor formulation.

Still referring to FIG. 1A and FIG. 1B, the reservoir 23 may be sized and configured to hold enough pre-vapor formulation such that the e-vaping device 60 may be configured for vaping for at least about 200 seconds. The e-vaping device 60 may be configured to allow each vaping to last a maximum of about 5 seconds.

The dispensing interface structure 24 may include a wicking material that includes filaments (or threads) having a capacity to draw one or more pre-vapor formulations. For example, a dispensing interface structure 24 may be a bundle of glass (or ceramic) filaments, a bundle including a group of windings of glass filaments, etc., all of which arrangements may be capable of drawing pre-vapor formulation through capillary action by interstitial spacings between the filaments. The filaments may be generally aligned in a direction perpendicular (transverse) or substantially perpendicular (e.g., perpendicular within the bounds of manufacturing techniques and/or tolerances and/or material tolerances) to the longitudinal direction of the e-vaping device 60. In some example embodiments, the dispensing interface structure 24 may include one to eight filament strands, each strand comprising a plurality of glass filaments twisted together. The end portions of the dispensing interface structure 24 may be flexible and foldable into the confines of one or more reservoirs 23. The filaments may have a cross-section that is generally cross-shaped, clover-shaped, Y-shaped, or in any other suitable shape.

The dispensing interface structure 24 may include any suitable material or combination of materials, also referred to herein as wicking materials. Examples of suitable materials may be, but not limited to, glass, ceramic- or graphite-based materials. The dispensing interface structure 24 may have any suitable capillary drawing action to accommodate pre-vapor formulations having different physical properties such as density, viscosity, surface tension and vapor pressure.

As described further below with reference to at least FIGS. 2A-2B, the dispensing interface structure 24 may, in some example embodiments, have at least one planar or substantially planar (e.g., planar within the bounds of manufacturing techniques and/or tolerances and/or material tolerances) surface. The dispensing interface structure 24 may be configured to contact the heater assembly 90 at the planar or substantially planar surface, so that the surface area of a portion of the dispensing interface structure 24 that is in contact with the heater assembly 90 is increased and/or maximized.

In some example embodiments, and as described further with regard to example embodiments illustrated in the following figures, the heater coil structure 94 may include a wire coil that may be at least partially in contact with at least one surface of the dispensing interface structure 24. The wire coil may be referred to as a heating coil wire. The heating coil wire may be a metal wire and/or the heating coil wire may extend fully or partially along one or more dimensions of the dispensing interface structure 24. The heater coil structure 94 may include a wire coil having one or more various cross-sectional area shapes (referred to herein as “cross sections”). For example, the heater coil structure 94 may include a wire coil comprising a wire that has at least one of a round cross section (e.g., at least one of a circular cross section, an oval cross section, an ellipse cross section, etc.), a polygonal cross section (e.g., at least one of a rectangular cross section, a triangular cross section, etc.), some combination thereof, or the like. In some example embodiments, the heater coil structure 94 may include a wire coil comprising a wire that has a substantially “flattened” shape.

The heater coil structure 94 may at least partially comprise any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heater coil structure 94 may at least partially comprise nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heater coil structure 94 may at least partially comprise at least one material selected from the group consisting of stainless steel, copper, copper alloys, nickel-chromium alloys, super alloys and combinations thereof. In some example embodiments, the heater coil structure 94 may at least partially comprise nickel-chromium alloys or iron-chromium alloys. In some example embodiments, the heater coil structure 94 may be a ceramic heater having an electrically resistive layer on an outside surface thereof.

The dispensing interface structure 24 may extend transversely across the central channel 30 between opposing portions of the reservoir 23. In some example embodiments, the dispensing interface structure 24 may extend parallel or substantially parallel (e.g., parallel within the bounds of manufacturing techniques and/or tolerances and/or material tolerances) to a longitudinal axis of the central channel 30. In some example embodiments, including the example embodiment illustrated in FIG. 1B, the dispensing interface structure 24 may extend orthogonally or substantially orthogonally (e.g., orthogonally within the bounds of manufacturing techniques and/or tolerances and/or material tolerances) to the longitudinal axis of the central channel 30.

In some example embodiments, the heater coil structure 94 is a porous material that incorporates a resistance heater formed of a material having a relatively high electrical resistance capable of generating heat relatively quickly.

In some example embodiments, the cartridge 70 may be replaceable. In other words, once the pre-vapor formulation of the cartridge 70 is depleted, only the cartridge 70 need be replaced. In some example embodiments, the entire e-vaping device 60 may be disposed once the reservoir 23 is depleted.

In some example embodiments, the e-vaping device 60 may be about 80 mm to about 110 mm long and about 7 mm to about 8 mm in diameter. For example, the e-vaping device 60 may be about 84 mm long and may have a diameter of about 7.8 mm.

FIG. 2A is a perspective view of a vaporizer assembly including a heater coil structure that defines a planar surface, according to some example embodiments. FIG. 2B is a cross-sectional view along line IIB-IIB' of the vaporizer assembly of FIG. 2A. The vaporizer assembly 88 illustrated in FIGS. 3A-B may be the vaporizer assembly 88 illustrated and described above with reference to FIGS. 1A-B.

Referring to FIGS. 2A-B, in some example embodiments, the vaporizer assembly 88 may include a heater assembly 90 that further includes a set of two electrical lead structures 92, a heater coil structure 94, and a non-conductive connector structure 96. The set of two electrical lead structures 92 includes separate electrical lead structures 92-1 and 92-2 that are coupled to opposite ends of the heater coil structure 94. The non-conductive connector structure 96 is connected to each of the electrical lead structures 92-1 and 92-2, such that the electrical lead structures 92-1 and 92-2 are coupled together independently of the heater coil structure 94.

As shown in FIGS. 2A-B, the electrical lead structures 92-1 and 92-2 are coupled to separate, respective electrical leads 26-1 and 26-2. The heater assembly 90 may thus be configured to receive a supply of electrical power through the coupled electrical leads 26-1 and 26-2 to induce an electrical current through the electrical lead structures 92-1 and 92-2 and the heater coil structure 94, independently of the non-conductive connector structure 96. The heater coil structure 94 may generate heat based on the electrical power supplied to the heater assembly 90, such that the heater assembly 90 is “activated.”

In some example embodiments, the electrical lead structures 92-1 and 92-2 are respective ends of the electrical leads 26-1 and 26-2. As a result, in some example embodiments, the electrical leads 26-1 and 26-2 are respectively connected to opposite ends of the heater coil structure 94, and the non-conductive connector structure 96 connects the electrical lead structures 92-1 and 92-2 together independently of the heater coil structure 94.

In some example embodiments, one or more of the electrical lead structures 92-1 and 92-2 is a rigid or substantially rigid (e.g., rigid within the bounds of manufacturing techniques and/or tolerances and/or material tolerances) post member that is separate from the electrical leads 26-1 and 26-2. The post member may have a cylindrical or substantially cylindrical (e.g., cylindrical within the bounds of manufacturing techniques and/or tolerances and/or material tolerances) shape. The post member may have a non-uniform, uniform, or substantially uniform cross-sectional area and/or shape along a longitudinal axis of the post member. For example, in the example embodiments illustrated in FIGS. 2A-B, electrical lead structure 92-1 has a proximate end that is connected to an end of the heater coil structure 94 and a distal end that is connected to electrical lead 26-1.

A cross-sectional area and/or shape of a post member comprising electrical lead structure 92-1 may be different at the proximate end of the post member, relative to the cross-sectional area and/or shape of the post member at the distal end of the power member. For example, in some example embodiments, including the example embodiments illustrated in FIGS. 2A-2B, a proximate portion of the post members comprising electrical lead structures 92-1 and 92-2 has a conical shape, relative to a distal portion of the post members that has a cylindrical or substantially cylindrical shape.

In some example embodiments, one or more portions of a post member comprising at least one of the electrical lead structures 92-1 and 92-2 may have one or more various cross-section area shapes. For example, in some example embodiments, the post member may have a rectangular cross-section shape, a square cross-section shape, a polygonal cross-section shape, an oval cross-section shape, an ellipse cross-section shape, some combination thereof, or the like.

In some example embodiments, the non-conductive connector structure 96 comprises one or more non-conductive or substantially non-conductive (e.g., insulating or substantially insulating) materials, where substantially non-conductive materials are non-conductive within the bounds of manufacturing techniques and/or tolerances and/or material tolerances and where substantially insulating materials are insulating within the bounds of manufacturing techniques and/or tolerances and/or material tolerances.

Examples of suitable materials that may at least partially comprise the non-conductive connector structure 96 include one or more metals, alloys, plastics or composite materials containing one or more of those materials. In some example embodiments, the non-conductive connector structure 96 may include one or more thermoplastics that are suitable for food or pharmaceutical applications. For example, the non-conductive connector structure 96 may include at least one of polypropylene, polyetheretherketone (PEEK), a ceramic material, low density polyethylene (LDPE), and high density polyethylene (HDPE).

The non-conductive connector structure 96 is configured to structurally connect the electrical lead structures 92-1 and 92-2 together, independently of the heater coil structure 94 and independently of establishing an electrical connection between the electrical lead structures 92-1 and 92-2 through the non-conductive connector structure 96.

In some example embodiments, including the example embodiments illustrated in FIGS. 2A-B, the heater assembly 90 is a rigid or substantially rigid structure, based at least in part upon the connection of the electrical lead structures 92-1 and 92-2 by the non-conductive connector structure 96. The heater assembly 90 may therefore be configured to transfer (e.g., conduct) a mechanical force (e.g., "load," "mechanical load," "force," etc.) therethrough. Thus, the heater assembly 90 may be a "load-bearing structure." As a result, the heater assembly 90 may be configured to apply a mechanical load to another structure.

In some example embodiments, including the example embodiments illustrated in FIGS. 2A-B, the heater assembly 90 is configured to contact a dispensing interface structure 24 through the heater coil structure 94, such that the heater assembly 90 is configured to heat pre-vapor formulation drawn from a reservoir by the dispensing interface structure 24. As shown in FIGS. 2A-B, the heater coil structure 94 is in contact with the surface 24*a* of the dispensing interface structure 24. The heater assembly 90 may heat pre-vapor formulation drawn from a reservoir by the dispensing interface structure 24, and thus held within the dispensing interface structure 24, based on generating heat at the heater coil structure 94 based on an electrical current induced in the electrical lead structures 92-1 and 92-2 and the heater coil structure 94. The heat generated at the heater coil structure 94 may be transferred to the dispensing interface structure 24 through conduction, such that the heat may be transferred to the pre-vapor formulation held within the dispensing interface structure 24.

In some example embodiments, the heater assembly 90 is configured to apply a mechanical load (e.g., a mechanical force) to one or more portions of the dispensing interface structure 24. As shown in FIGS. 2A-B, for example, the heater assembly 90 is configured to apply a mechanical force 89-1 to the dispensing interface structure 24, based on contact between the heater coil structure 94 and a surface 24*a* of the dispensing interface structure 24. As shown in FIGS. 2A-B, the heater assembly 90 and the dispensing interface structure 24 may be in compression based on the mechanical force 89 applied to the dispensing interface structure 24 through the heater coil structure 94. As further shown in FIGS. 2A-B, the electrical lead structures 92-1 and 92-2 may be in compression 89-2 based on the heater assembly 90 applying a mechanical force 89-1 to the dispensing interface structure 24 through at least the heater coil structure 94.

In some example embodiments, by applying a mechanical load to the dispensing interface structure 24 through the heater coil structure 94 so that the heater assembly 90 is in compression with the dispensing interface structure 24, the heater assembly 90 may be configured to enable improved contact between at least the heater coil structure 94 of the heater assembly 90 and the dispensing interface structure 24. Such improved contact may result in improved heat transfer between the heater assembly 90 and the dispensing interface structure 24.

In some example embodiments, the heater assembly 90 may be at least partially coupled to a surface of the dispensing interface structure 24 by one or more adhesive materials. For example, in some example embodiments, the heater coil structure 94 may be at least partially coupled to the dispensing interface structure 24 by one or more adhesive materials.

In some example embodiments, including the example embodiments illustrated in FIGS. 2A-B, the heater coil structure 94 is configured to define a surface 98, and the heater assembly 90 is configured to apply a mechanical force to the dispensing interface structure 24, such that the heater coil structure 94 defines a surface 98 substantially flush (e.g., flush within the bounds of manufacturing techniques and/or tolerances and/or material tolerances) with a surface 24*a* of the dispensing interface structure 24. As shown in the example embodiments illustrated in FIGS. 2A-B, for example, the heater coil structure 94 defines a planar or substantially planar surface 98 and the dispensing interface structure 24 has a planar or substantially planar surface 24*a*. Thus, the heater coil structure 94 maybe understood to define a surface 98 that is complementary to the surface 24*a* of the dispensing interface structure 24. The heater assembly 90 may be configured to contact the dispensing interface structure 24, through contact of the heater coil structure 94 with the planar or substantially planar surface 24*a* of the dispensing interface structure 24, such that the defined surface 98 of the heater coil structure 94 is flush or substantially flush with the complementary surface 24*a* of the dispensing interface structure 24.

In some example embodiments, the heater coil structure 94 defines one or more patterns. In the example embodiments illustrated in FIGS. 2A-B, for example, the heater coil structure 94 defines a spiral pattern, where the electrical lead structures 92-1 and 92-2 are coupled to opposite ends of the heater coil structure 94. It will be understood that the patterns defined by the heater coil structure 94 are not limited to the patterns illustrated in FIGS. 2A-B.

In some example embodiments, the dispensing interface structure 24 may have a surface that is configured to increase and/or maximize the surface area of the surface 24*a* to which the heater assembly 90 is in contact. In the example embodiments illustrated in FIGS. 2A-B, the surface 24*a* is planar or substantially planar (e.g., planar within the bounds of manufacturing techniques and/or tolerances and/or material tolerances). In some example embodiments, the surface 24*a* is a three-dimensional surface that has an increased total surface area, relative to a planar or substantially planar surface.

Figure 3A:
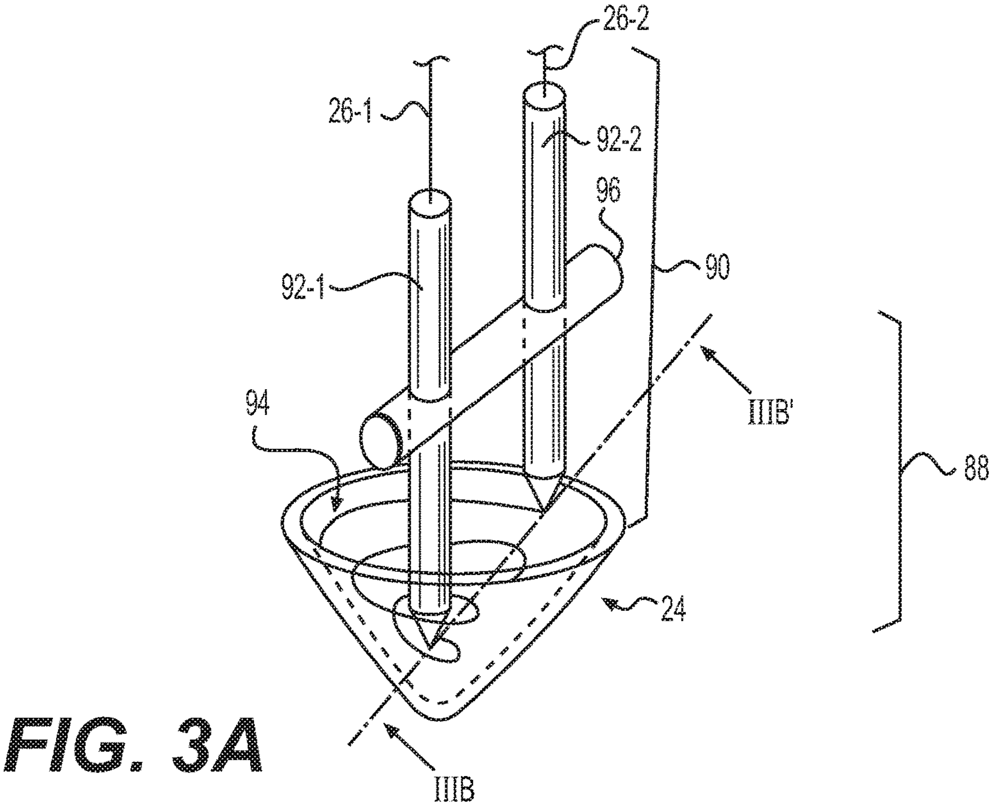
FIG. 3A is a perspective view of a vaporizer assembly including a heater coil structure that defines a substantially conical surface, according to some example embodiments.
Figure 3B:
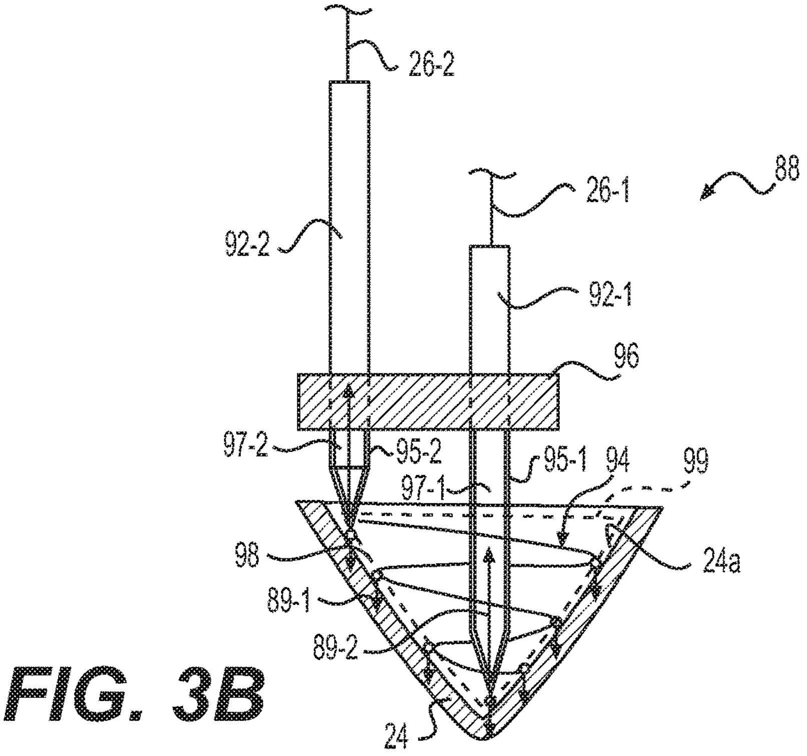
FIG. 3B is a cross-sectional view along line IIIB-IIIB' of the vaporizer assembly of FIG. 3A.

FIG. 3A is a perspective view of a vaporizer assembly including a heater coil structure that defines a substantially conical (e.g., conical within the bounds of manufacturing techniques and/or tolerances and/or material tolerances) 3-D surface, according to some example embodiments. FIG. 3B is a cross-sectional view along line IIIB-IIIB' of the vaporizer assembly of FIG. 3A. The vaporizer assembly 88 illustrated in FIGS. 3A-B may be the vaporizer assembly 88 illustrated and described above with reference to FIGS. 1A-B.

In some example embodiments, the heater assembly 90 includes a heater coil structure 94 that is shaped such that the heater coil structure 94 defines a three-dimensional (3-D) surface. Such a 3-D surface may include a conical or substantially conical surface.

In some example embodiments, a heater assembly 90 including a heater coil structure 94 that defines a 3-D shaped surface 98 (e.g., 3-D surface) may be configured to provide improved contact between the heater assembly 90 and a surface 24*a* of the dispensing interface structure 24. In the example embodiments illustrated in FIGS. 3A-B, for example, the heater coil structure 94 defines a conical spiral pattern that substantially defines (e.g., defines within the bounds of manufacturing techniques and/or tolerances and/or material tolerances) a conical or substantially conical 3-D surface 98. A heater coil structure 94 that defines a conical or substantially conical 3-D surface 98 may be configured to have improved physical contact with a complementary conical or substantially conical surface 24*a* of the dispensing interface structure 24. Improved physical contact may enable improved heat transfer between the heater assembly 90 and the dispensing interface structure 24.

In some example embodiments, the dispensing interface structure 24 has a 3-D shape that at least partially defines an interior space 99 such that surface 24*a* is a 3-D surface that at least partially defines the interior space 99. As shown in FIGS. 3A-B, for example, the dispensing interface structure 24 may be a 3-D structure that defines a conical or substantially conical 3-D shape, such that the surface 24*a* is a conical or substantially conical 3-D surface. The surface 24*a* may be the same or substantially the same (e.g., the same within the bounds of manufacturing techniques and/or tolerances and/or material tolerances) as the 3-D surface 98 defined by the heater coil structure 94. Thus, if and/or when the heater coil structure 94 is in contact with surface 24*a* of the dispensing interface structure 24, the heater coil structure 94 defines a surface 98 that may be in flush or substantially flush contact with the surface 24*a* of the dispensing interface structure 24.

In some example embodiments, the opposite ends of the heater coil structure 94 may be located at different planes orthogonal to the longitudinal axes of the electrical lead structures 92-1 and 92-2, instead of the opposite ends of the heater coil structure 94 that are located in a common plane orthogonal to the longitudinal axes of the electrical lead structures 92-1 and 92-2 as illustrated in FIGS. 2A-B. In some example embodiments, the electrical lead structures 92-1 and 92-2 are coupled to opposite ends of the heater coil structure 94.

As a result, and as shown in FIGS. 3A-B, if and/or when a surface 24*a* of the dispensing interface structure 24 at least partially defines an interior space 99, at least one of the electrical lead structures 92-1 may extend further into the interior space 99 than another one of the electrical lead structures 92-1 if and/or when the heater coil structure 94 is in flush or substantially flush contact (e.g., flush contact within the bounds of manufacturing techniques and/or tolerances and/or material tolerances) with the surface 24*a*.

For example, in the example embodiments illustrated in FIGS. 3A-B, the electrical lead structures 92-1 and 92-2 are coupled to opposite ends of the heater coil structure 94 at different planes that are orthogonal to the longitudinal axes of the electrical lead structures 92-1 and 92-2. The electrical lead structure 92-1 is coupled to an end of the heater coil structure 94 that is at the vertex of the conical or substantially conical surface 98 defined by the heater coil structure 94, and the electrical lead structure 92-1 is coupled to an end of the heater coil structure 94 that is at an edge of the surface 98 defined by the heater coil structure 94. As a result, if and/or when the heater assembly 90 is in contact with the dispensing interface structure 24 such that the heater coil structure 94 is in flush or substantially flush contact with surface 24*a*, the electrical lead structure 92-1 may extend further into the interior space 99 than the electrical lead structure 92-2.

In some example embodiments, the dispensing interface structure 24 includes one or more surfaces 24*a* that define one or more shapes that are the same or substantially the same as the one or more shapes of a surface 98 defined by the heater coil structure 94. As a result, the one or more surfaces 24*a* and the one or more surfaces 98 defined by the heater coil structure 94 may be understood to be "complementary" surfaces.

In some example embodiments, a heater coil structure 94 that defines a 3-D surface may contact one or more surfaces 24*a* of the dispensing interface structure 24, where the one or more surfaces 24*a* are complementary to the surface 98 defined by the heater coil structure 94. As a result, at least a portion of the heater coil structure 94 that is in contact with the dispensing interface structure 24 may be in flush or substantially flush contact with the one or more surfaces 24*a* of the dispensing interface structure 24.

As shown in FIGS. 3A-B, the heater assembly 90 may exert a mechanical force 89-1 on the dispensing interface structure 24 through the heater coil structure 94 that is in contact with the surface 24*a* of the dispensing interface structure 24, such that the dispensing interface structure 24 is in compression with the heater coil structure 94 and the electrical lead structures 92-1 and 92-2 are in compression 89-2. As noted above, such compressive force may improve contact, and thus heat transfer communication, between the heater coil structure 94 and the dispensing interface structure 24, thereby improving the transfer of heat to pre-vapor formulation held within the dispensing interface structure 24 to enable improved vapor generation efficiency.

In some example embodiments, the electrical lead structures 92-1 and 92-2 are configured to mitigate a probability of an electrical short therebetween. For example, as shown in the example embodiments illustrated in FIGS. 3A-B, the electrical lead structures 92-1 and 92-2 may include surface portions 95-1 and 95-2 that may be associated with a reduced electrical conductivity, relative to remainder interior portions 97-1 and 97-2 of the electrical lead structures 92-1 and 92-2, respectively. In some example embodiments, the surface portions 95-1 and 95-2 may be oxidized, in relation to the interior portions 97-1 and 97-2, such that the one or more surface portions 95-1 and 95-2 have a reduced electrical conductivity in relation to the interior portions 97-1 and 97-2 and the electrical lead structures 92-1 and 92-2 are configured to mitigate a probability of an electrical short therebetween.

In some example embodiments, the electrical lead structures 92-1 and 92-2 are configured to mitigate a probability of an electrical short therebetween through the dispensing interface structure 24. For example, as described further below, one or more of the electrical lead structures 92-1 and 92-2 may at least partially extend through an interior of the dispensing interface structure 24. One or more of the electrical lead structures 92-1 and 92-2 at least partially extending through an interior of the dispensing interface structure 24 may include an at least partially oxidized outer surface, such that the one or more electrical lead structures 92-1 and 92-2 are configured to mitigate a probability of an electrical short through an interior of the dispensing interface structure 24 between the electrical lead structures 92-1 and 92-2.

As shown in FIGS. 3A-B, some example embodiments include a heater assembly 90 that at least partially extends into the interior space 99 at least partially defined by the dispensing interface structure 24, such that the heater coil structure 94 contacts a surface 24*a* of the dispensing interface structure 24 that at least partially defines the interior space 99.

Figure 4A:
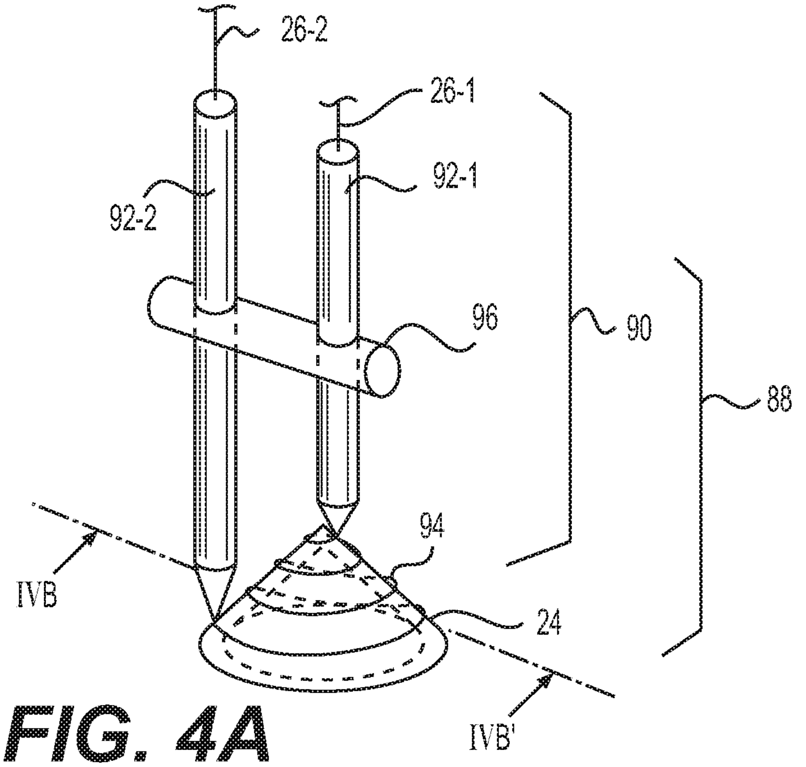
FIG. 4A is a perspective view of a vaporizer assembly including a heater coil structure that defines a substantially conical surface, according to some example embodiments.
Figure 4B:
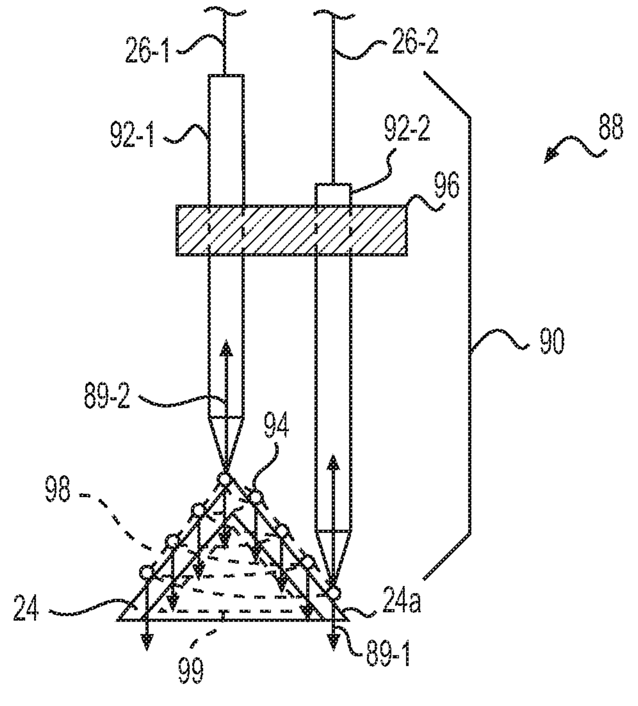
FIG. 4B is a cross-sectional view along line IVB-IVB' of the vaporizer assembly of FIG. 4A.

FIG. 4A is a perspective view of a vaporizer assembly including a heater coil structure that defines a substantially conical surface, according to some example embodiments. FIG. 4B is a cross-sectional view along line IVB-IVB' of the vaporizer assembly of FIG. 4A. The vaporizer assembly 88 illustrated in FIGS. 4A-B may be the vaporizer assembly 88 illustrated and described above with reference to FIGS. 1A-B.

In some example embodiments, a dispensing interface structure surface 24*a* and a surface 98 defined by the heater coil structure 94 may have complementary shapes. In the example embodiments illustrated in FIGS. 4A-B, for example, the heater coil structure 94 and dispensing interface structure 24 respectively define complementary 3-D conical surfaces 98 and 24*a*, such that the heater assembly 90 is configured to contact a surface 24*a* of the dispensing interface structure 24 that is distal from a surface 24*b* of the dispensing interface structure 24 defining an interior space 99. As shown in FIGS. 4A-B, the surface 98 defined by the heater coil structure 94 may be complementary with the surface 24*a*, such that the heater coil structure 94 may be in flush or substantially flush contact with the surface 24*a* of the dispensing interface structure 24 that is in contact with the heater coil structure 94.

As further shown in FIGS. 4A-B, the heater assembly 90 may exert a compressive mechanical force 89-1 on the dispensing interface structure 24, such that the electrical lead structures 92-1 and 92-2 are in compression 89-2, to improve contact between the heater coil structure 94 and the dispensing interface structure 24.

Figure 5A:
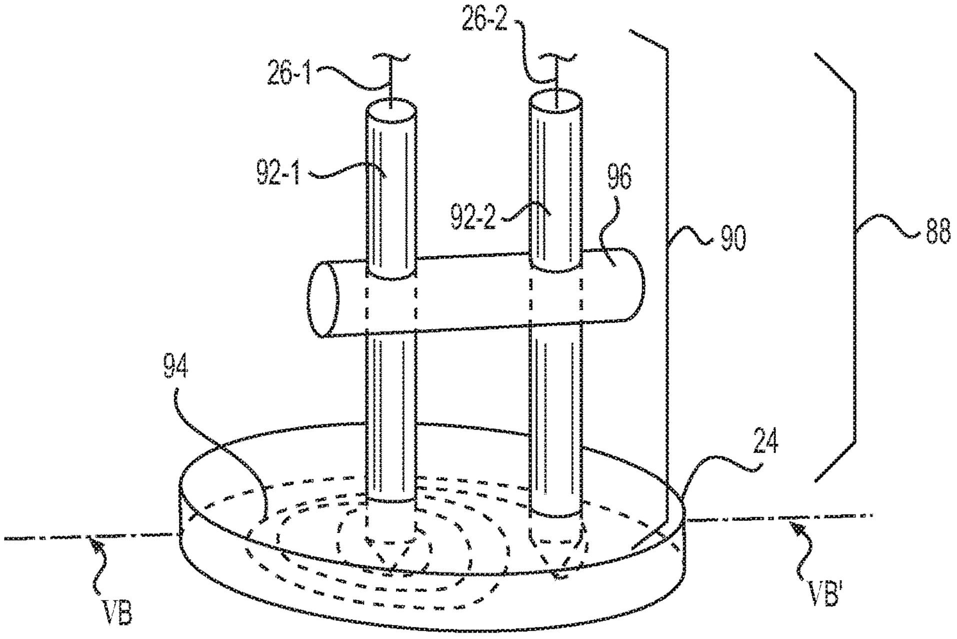
FIG. 5A is a perspective view of a vaporizer assembly including a dispensing interface structure between the heater coil structure and the non-conducting connector structure, according to some example embodiments.
Figure 5B:
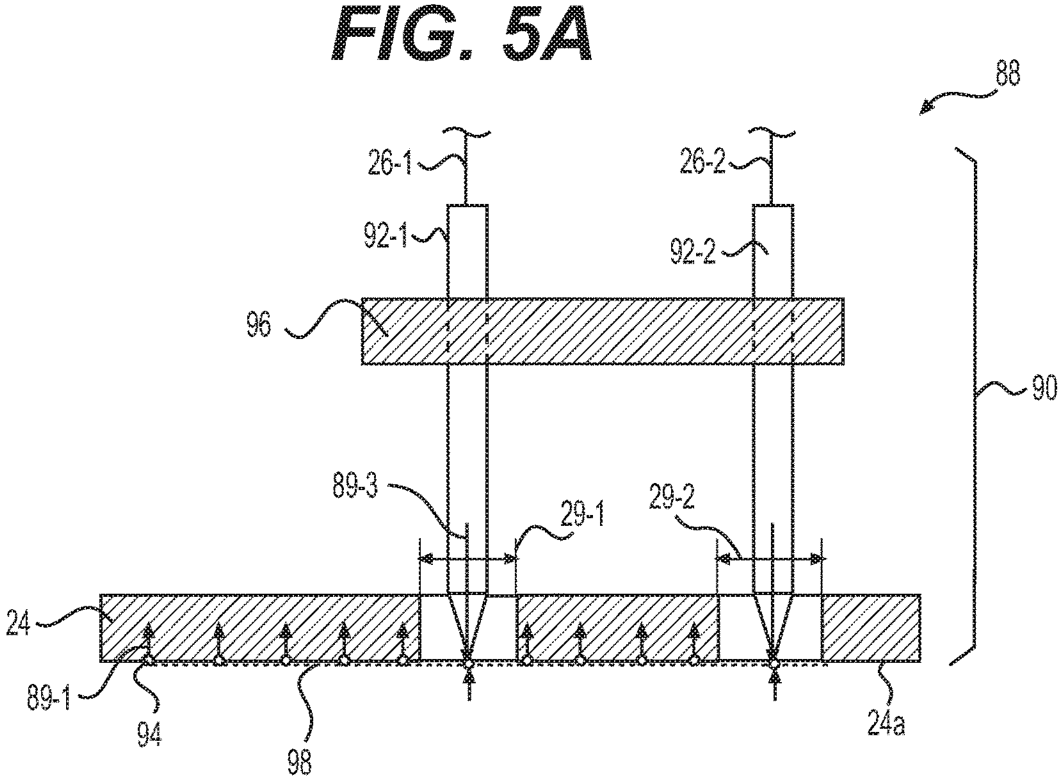
FIG. 5B is a cross-sectional view along line VB-VB' of the vaporizer assembly of FIG. 5A.

FIG. 5A is a perspective view of a vaporizer assembly including a dispensing interface structure between the heater coil structure and the non-conducting connector structure, according to some example embodiments. FIG. 5B is a cross-sectional view along line VB-VB' of the vaporizer assembly of FIG. 5A. The vaporizer assembly 88 illustrated in FIGS. 5A-B may be the vaporizer assembly 88 illustrated and described above with reference to FIGS. 1A-B.

In some example embodiments, the heater assembly 90 is configured to contact a dispensing interface structure 24 that is between the heater coil structure 94 and the non-conductive connector structure 96. As a result, the heater assembly 90 may exert a compressive mechanical force 89-1 on the dispensing interface structure 24 such that the heater coil structure 94 is in compression with a surface 24*a* of the dispensing interface structure 24 and the electrical lead structures 92-1 and 92-2 are in tension 89-3. The electrical lead structures 92-1 and 92-2 may exert a pulling force on the heater coil structure 94 to cause the heater coil structure 94 to be pressed into the surface 24*a* of the dispensing interface structure 24. The surface 24*a*, in the example embodiments shown in FIGS. 5A-B, is a distal surface relative to the heater assembly 90.

As further shown in FIGS. 5A-B, the dispensing interface structure 24 may include gaps 29-1 and 29-2 through which the electrical lead structures 92-1 and 92-2 may extend, respectively, such that the electrical lead structures 92-1 and 92-2 extend through the distal surface 24*a* of the dispensing interface structure 24 to couple with a heater coil structure 94. As a result, the dispensing interface structure 24 is between the heater coil structure 94 and the non-conductive connector structure 96.

The electrical lead structures 92-1 and 92-2 may be in tension 89-3, such that the electrical lead structures 92-1 and 92-2 pull the heater coil structure 94 into contact with the distal surface 24*a* of the dispensing interface structure 24 to hold the heater coil structure 94 in compression with the dispensing interface structure 24.

In the example embodiments illustrated in FIGS. 5A-B, the dispensing interface structure 24 and the heater coil structure 94 have and define complementary planar or substantially planar surfaces 24*a* and 98, respectively. However, it will be understood that a dispensing interface structure 24 that is between the heater coil structure 94 and the non-conductive connector structure 96 may have surfaces having various shapes, including any of the surfaces described herein.

As further described above, the electrical lead structures 92-1 and 92-2 may be at least partially configured to at least partially mitigate electrical shorting between the electrical lead structures 92-1 and 92-2 through the interior of the dispensing interface structure 24. For example, at least the respective portions of the electrical lead structures 92-1 and 92-2 that extend through the interior space defined by the dispensing interface structure 24 may include surface portions 95-1 and 95-2 that have reduced electrical conductivity relative to respective interior portions 97-1 and 97-2 thereof.

Figure 6A:
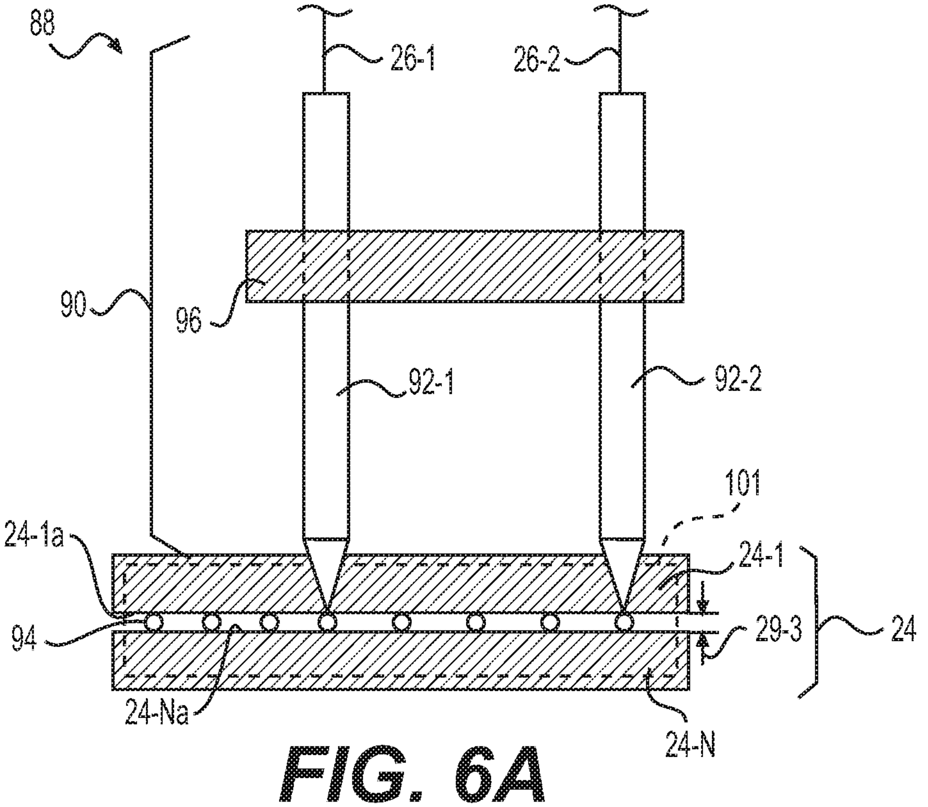
FIG. 6A is a cross-sectional view of a vaporizer assembly including a heater coil structure within an interior space of a dispensing interface structure, according to some example embodiments.
Figure 6B:
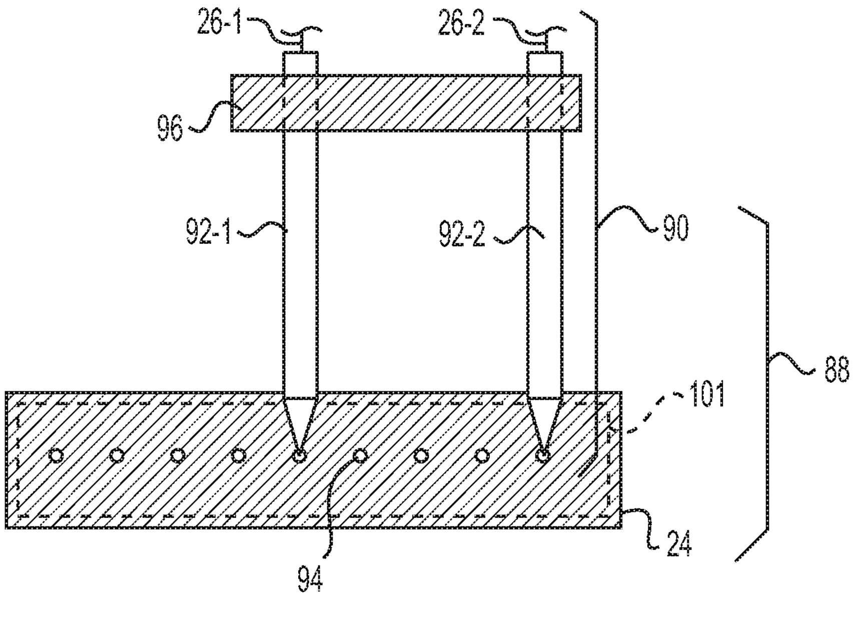
FIG. 6B is a cross-sectional view of a vaporizer assembly including a heater coil structure within an interior space of a dispensing interface structure, according to some example embodiments.

FIG. 6A is a cross-sectional view of a vaporizer assembly including a heater coil structure within an interior space of a dispensing interface structure, according to some example embodiments. FIG. 6B is a cross-sectional view of a vaporizer assembly including a heater coil structure within an interior space of a dispensing interface structure, according to some example embodiments. The vaporizer assembly 88 illustrated in FIGS. 5A-B may be the vaporizer assembly 88 illustrated and described above with reference to FIGS. 1A-B.

In some example embodiments, a vaporizer assembly 88 includes a heater assembly 90 that is configured to contact the dispensing interface structure 24 such that the heater coil structure 94 is at least partially within an interior space 101 of the dispensing interface structure 24.

As shown in the example embodiments illustrated in FIGS. 6A-B, for example, a vaporizer assembly 88 may include a heater assembly 90 that is at least partially within an interior space 101 of the dispensing interface structure 24, such that the heater coil structure 94 is within the interior space 101 and is in contact with one or more portions of the dispensing interface structure 24.

In some example embodiments, a dispensing interface structure 24 may include multiple sub-structures that define an interior space 101 of the dispensing interface structure 24, and the heater coil structure 94 may be between two or more of the sub-structures such that the heater coil structure 94 is within the defined interior space 101. In the example embodiments illustrated in FIG. 6A, for example, the dispensing interface structure 24 includes multiple sub-structures 24-1 to 24-N that collectively define an interior space 101 of the dispensing interface structure 24, where such an interior space 101 includes the space occupied by the sub-structures 24-1 to 24-N and a gap space 29-3 that is between the sub-structures 24-1 to 24-N such that the gap space 29-3 is at least partially defined by the respective interior surfaces 24-1*a* to 24-Na of the sub-structures 24-1 to 24-N. As shown in FIG. 6A, the heater assembly 90 may include a heater coil structure 94 that is located at least partially within the gap space 29-3. The heater coil structure 94 may be at least partially in contact with one or more of the surfaces 24-1*a* to 24-Na of the sub-structures 24-1 to 24-N that at least partially define the gap space 29-3. The electrical lead structures 92-1 and 92-2 may extend through one or more sub-structures and/or between two or more sub-structures to the gap space 29-3.

In some example embodiments, a heater assembly 90 includes a heater coil structure 94 that is at least partially enclosed within a structure of a dispensing interface structure 24 and one or more electrical lead structures 92-1 and 92-2 that at least partially extend through the dispensing interface structure 24. For example, as shown in the example embodiments illustrated in FIG. 6B, the heater coil structure 94 and at least a portion of the electrical lead structures 92-1 and 92-2 are enclosed within the interior space 101 of the dispensing interface structure 24. As a result, in the example embodiments illustrated in FIG. 6B, an entirety or substantially an entirety (e.g., an entirety within the bounds of manufacturing techniques and/or tolerances and/or material tolerances) of the heater coil structure 94 that is exposed from the electrical lead structures 92-1 and 92-2 may be in contact with one or more portions of the dispensing interface structure 24, thereby being configured to provide improved heat transfer from the heater assembly 90 to pre-vapor formulation held within the dispensing interface structure 24.

Figure 7A:
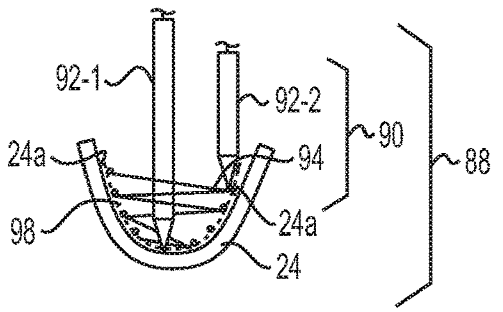
FIG. 7A is a cross-sectional view of a vaporizer assembly including a heater coil structure that defines a substantially paraboloid surface, according to some example embodiments.
Figure 7B:
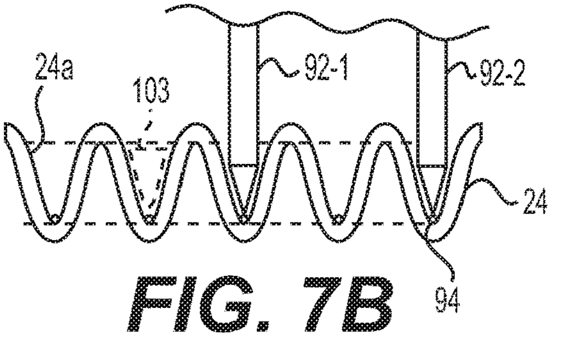
FIG. 7B is a cross-sectional view of a vaporizer assembly including a heater coil structure that contacts a dispensing interface structure that has a variable cross-section, according to some example embodiments.
Figure 8A:
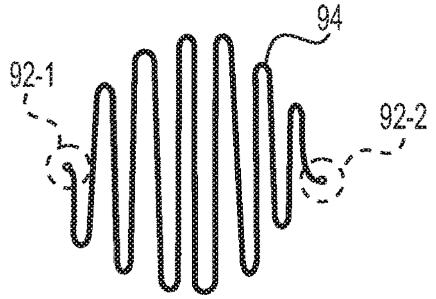
FIG. 8A is a plan view of a heater coil structure that defines a sinusoidal pattern, according to some example embodiments.
Figure 8B:
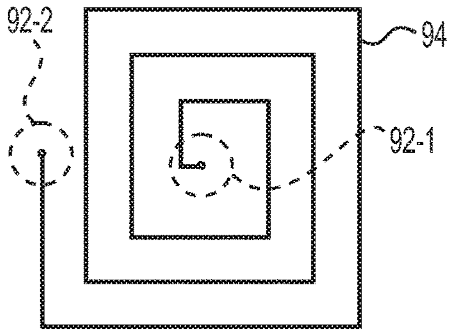
FIG. 8B is a plan view of a heater coil structure that defines a polygonal spiral pattern, according to some example embodiments.

FIG. 7A is a cross-sectional view of a vaporizer assembly including a heater coil structure that defines a substantially paraboloid (e.g., paraboloid within the bounds of manufacturing techniques and/or tolerances and/or material tolerances) surface, according to some example embodiments. FIG. 7B is a cross-sectional view of a vaporizer assembly including a heater coil structure that contacts a dispensing interface structure that has a variable cross-section, according to some example embodiments. FIG. 8A is a plan view of a heater coil structure that defines a sinusoidal pattern, according to some example embodiments. FIG. 8B is a plan view of a heater coil structure that defines a polygonal spiral pattern, according to some example embodiments.

In some example embodiments, the heater coil structure 94 and dispensing interface structure 24 may define and have one or more various complementary 3-D surfaces, respectively.

In the example embodiments illustrated in FIG. 7A, for example, the heater coil structure 94 and dispensing interface structure 24 may define and have complementary paraboloid surfaces 98 and 24*a*, respectively. Complementary surfaces 98, 24*a* that may be defined by the heater coil structure 94 and included in the dispensing interface structure 24, respectively, may include any planar or substantially planar surface and may include any 3-D surface, including any 3-D surface that may be defined by one or more multivariable equations. The complementary surfaces may be any quadric surface.

In some example embodiments, the dispensing interface structure 24 has a surface 24*a* that further defines a pattern that is substantially complementary (e.g., complementary within the bounds of manufacturing techniques and/or tolerances and/or material tolerances) to a pattern defined by the heater coil structure 94. Such a surface 24*a* may be referred to as a corrugated surface, where the corrugation pattern thereof is substantially complementary to the pattern defined by the heater coil structure 94. For example, in the example embodiments illustrated in FIG. 7B, where the heater coil structure 94 defines a spiral pattern, the dispensing interface structure 24 may have a surface 24*a* defining a valley region 103 that defines a spiral pattern that is substantially complementary to the spiral pattern defined by the heater coil structure 94. The dispensing interface structure 24 may thus be referred to as having a spiral corrugated surface 24*a* where the spiral corrugations thereof are in a pattern that is substantially complementary to the spiral pattern defined by the heater coil structure 94. As a result, as shown in FIG. 7B, the heater coil structure 94 may contact the dispensing interface structure 24 in flush or substantially flush contact with a trough portion of the valley region 103 defined by the surface 24*a*.

In some example embodiments, the heater coil structure 94 may define one or more various patterns. In the example embodiments illustrated in FIGS. 2A-7B, for example, the heater coil structure 94 defines a spiral pattern.

It will be understood that the heater coil structure 94 may define various patterns. In the example embodiments shown in FIG. 8A, for example, the heater coil structure 94 defines a sinusoidal pattern. In the example embodiments shown in FIG. 8B, the heater coil structure 94 defines a rectangular spiral pattern.

The heater coil structure 94 may be included in a heater assembly 90 that is in contact with a dispensing interface structure 24 defining a substantially similar (e.g., similar within the bounds of manufacturing techniques and/or tolerances and/or material tolerances) pattern, such that the heater coil structure 94 is in contact with a peak or trough portion of the dispensing interface structure 24 corresponding to the complementary pattern defined thereby.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

I claim:

1. A vaporizer assembly for an e-vaping device, the vaporizer assembly comprising:

a heater coil structure;

a set of two electrical lead structures, the electrical lead structures coupled to opposite ends of the heater coil structure; and a non-conductive connector structure connected to each of the electrical lead structures, such that the electrical lead structures are coupled together independently of the heater coil structure, wherein the vaporizer assembly is configured to contact a dispensing interface structure through the heater coil structure, such that the vaporizer assembly is configured to heat pre-vapor formulation drawn from a reservoir by the dispensing interface structure, wherein the vaporizer assembly is configured to apply a mechanical force to the dispensing interface structure through the electrical lead structures and the heater coil structure, such that both the heater coil structure and the electrical lead structures are in compression with the dispensing interface structure, and a surface of the heater coil structure is substantially flush with a surface of the dispensing interface structure.

2. The vaporizer assembly of claim 1, wherein the heater coil structure defines a three-dimensional (3-D) surface.

3. The vaporizer assembly of claim 2, wherein the 3-D surface is a substantially conical surface.

4. The vaporizer assembly of claim 1, wherein, at least one electrical lead structure, of the set of two electrical lead structures, includes an interior portion and a surface portion, and the surface portion is associated with a reduced conductivity, in relation to the interior portion.

5. A cartridge for an e-vaping device, the cartridge comprising:

a reservoir configured to hold a pre-vapor formulation;

a dispensing interface structure coupled to the reservoir, the dispensing interface structure configured to draw the pre-vapor formulation from the reservoir; and a vaporizer assembly in contact with the dispensing interface structure, the vaporizer assembly configured to heat the drawn pre-vapor formulation, the vaporizer assembly including, a heater coil structure, a set of two electrical lead structures, the electrical lead structures coupled to opposite ends of the heater coil structure, and a non-conductive connector structure connected to each of the electrical lead structures, such that the electrical lead structures are coupled together independently of the heater coil structure, wherein the vaporizer assembly is configured to contact the dispensing interface structure through the heater coil structure, wherein the vaporizer assembly is configured to apply a mechanical force to the dispensing interface structure through the electrical lead structures and the heater coil structure, such that both the heater coil structure and the electrical lead structures are in compression, and a surface of the heater coil structure is substantially flush with a surface of the dispensing interface structure.

6. The cartridge of claim 5, wherein the heater coil structure defines a three-dimensional (3-D) surface.

7. The cartridge of claim 6, wherein the 3-D surface is a substantially conical surface.

8. The cartridge of claim 5, wherein, at least one electrical lead structure, of the set of two electrical lead structures, includes an interior portion and a surface portion, and the surface portion is associated with a reduced conductivity, in relation to the interior portion.

9. An e-vaping device, comprising:

a cartridge, including, a reservoir configured to hold a pre-vapor formulation;

a dispensing interface structure coupled to the reservoir, the dispensing interface structure configured to draw the pre-vapor formulation from the reservoir; and a vaporizer assembly in contact with the dispensing interface structure, the vaporizer assembly configured to heat the drawn pre-vapor formulation, the vaporizer assembly including, a heater coil structure, a set of two electrical lead structures, the electrical lead structures coupled to opposite ends of the heater coil structure, and a non-conductive connector structure connected to each of the electrical lead structures, such that the electrical lead structures are coupled together independently of the heater coil structure; and a power supply section coupled to the cartridge, the power supply section configured to supply electrical power to the vaporizer assembly, wherein the vaporizer assembly is configured to contact the dispensing interface structure through the heater coil structure, wherein the vaporizer assembly is configured to apply a mechanical force to the dispensing interface structure through the electrical lead structures and the heater coil structure, such that both the heater coil structure and the electrical lead structures are in compression, and a surface of the heater coil structure is substantially flush with a surface of the dispensing interface structure.

10. The e-vaping device of claim 9, wherein the heater coil structure defines a three-dimensional (3-D) surface.

11. The e-vaping device of claim 10, wherein the 3-D surface is a substantially conical surface.

12. The e-vaping device of claim 9, wherein the power supply section includes a rechargeable battery.

13. The e-vaping device of claim 9, wherein the cartridge and the power supply section are removably coupled together.

14. The e-vaping device of claim 9, wherein, at least one electrical lead structure, of the set of two electrical lead structures, includes an interior portion and a surface portion, and the surface portion is associated with a reduced conductivity, in relation to the interior portion.

* * * * *